United States Patent [19]
Ciamacco, Jr.

[11] Patent Number: 6,093,142
[45] Date of Patent: Jul. 25, 2000

[54] DEVICE FOR IN VIVO RADIATION DELIVERY AND METHOD FOR DELIVERY

[75] Inventor: Sam Ciamacco, Jr., San Diego, Calif.

[73] Assignee: MedTronic Inc., Minneapolis, Minn.

[21] Appl. No.: 09/070,701

[22] Filed: Apr. 30, 1998

[51] Int. Cl.$^7$ ...................................................... A61N 5/00
[52] U.S. Cl. .................. 600/3; 604/96; 606/194
[58] Field of Search .............................. 600/1–8; 604/96, 604/102, 103; 606/7, 192, 194, 195

[56] References Cited

U.S. PATENT DOCUMENTS

| | | | |
|---|---|---|---|
| 3,324,847 | 6/1967 | Zoumboulis . | |
| 5,199,939 | 4/1993 | Dake et al. | 600/3 |
| 5,213,561 | 5/1993 | Weinstein | 600/7 |
| 5,429,582 | 7/1995 | Williams | 600/2 |
| 5,484,384 | 1/1996 | Fearnot | 600/3 |
| 5,540,659 | 7/1996 | Teirstein | 604/104 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,643,171 | 7/1997 | Bradshaw et al. | 600/1 |
| 5,662,580 | 9/1997 | Bradshaw et al. | 600/3 |

FOREIGN PATENT DOCUMENTS

| | | |
|---|---|---|
| 688580 | 6/1994 | European Pat. Off. . |
| WO 95/26681 | 10/1995 | WIPO . |

OTHER PUBLICATIONS

*Handbook of Adhesives*, edited by I. Skeist, (3$^{rd}$ ed., Chapman & Hall, NY, 1990), p. 7.

*Primary Examiner*—John P. Lacyk

[57] ABSTRACT

A method and an apparatus are provided for delivery of radiation in vivo. A device includes a seal located proximal to a balloon through which a cavity of the balloon is inflated with a composition including a radioactive compound. Preferably, the seal includes a first passage provides access for the inflation tubing through the seal which, at the distal end, terminates at a location within the balloon cavity. A second passage, also included in the seal, provides access for the flushing tubing which, at the distal end, terminates at the proximal end of the balloon. These passages through the seal isolate the radioactive material source from a flushing mechanism. In such a construction, inflation and evacuation can be accomplished without contamination of the entire medical device lumen. Thus, substantially all of the solution including the radioactive compound can be evacuated and the balloon cavity can be subsequently flushed or rinsed to remove substantially all the radioactive compound after treatment due to the positioning of the passage in the seal.

19 Claims, 5 Drawing Sheets

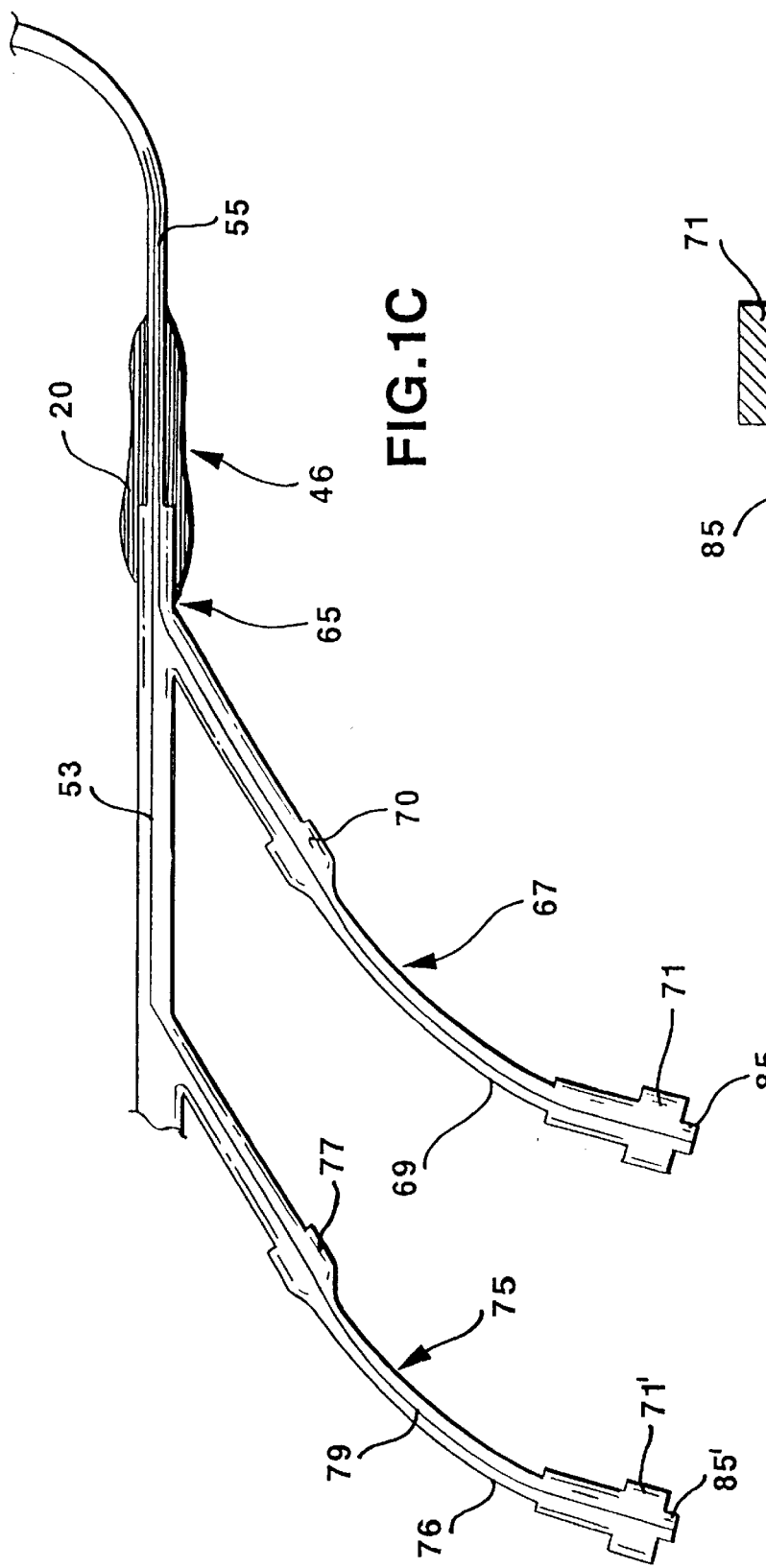
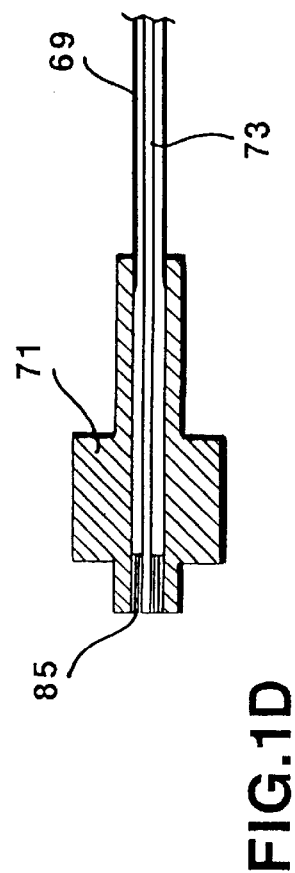
FIG.1C
FIG.1D

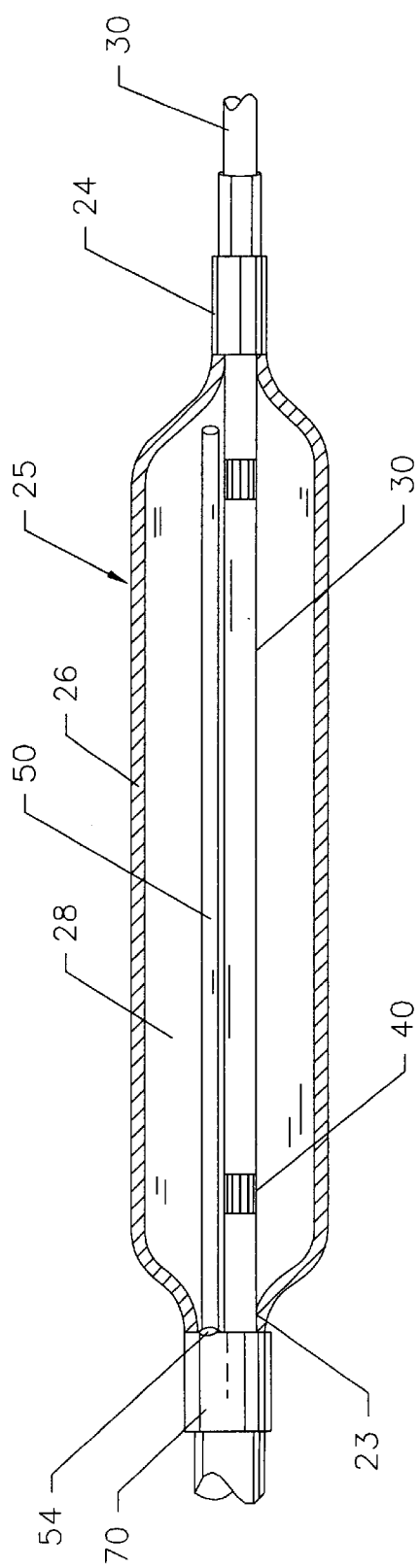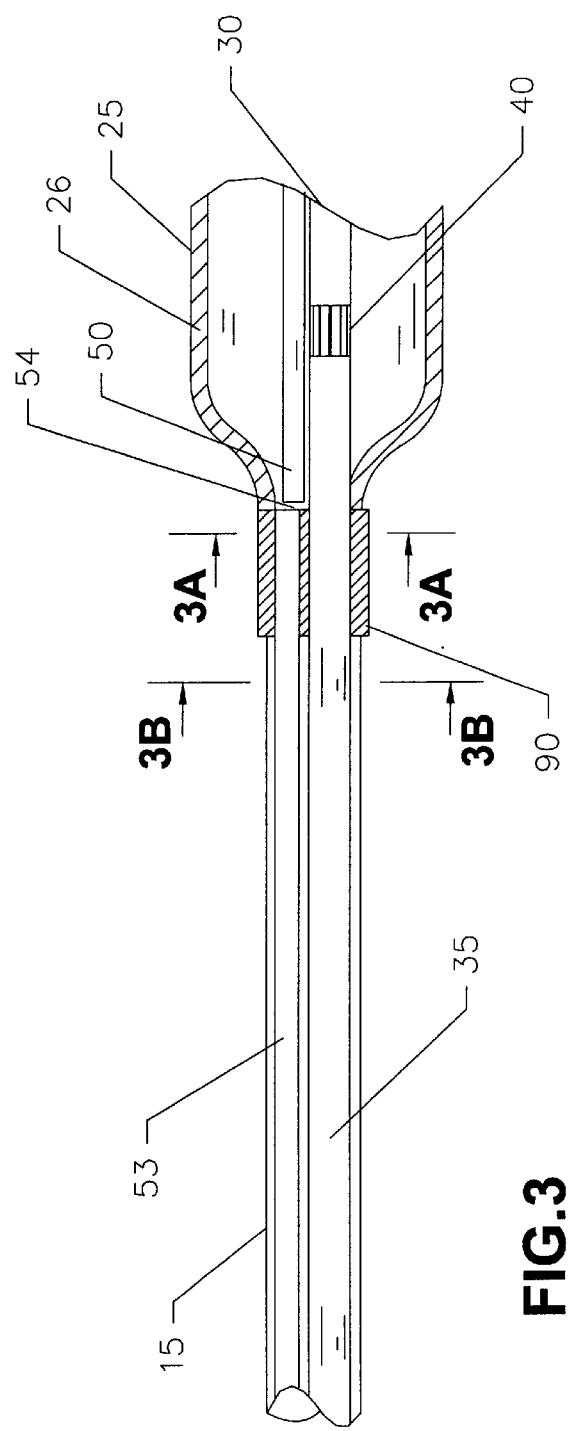

DEVICE FOR IN VIVO RADIATION DELIVERY AND METHOD FOR DELIVERY

FIELD OF THE INVENTION

The present invention relates to radiation delivery device and more particularly to a dual lumen catheter for delivery of a radioactive material for delivering localized radiation in vivo. Also provided is a method for delivering localized radiation in vivo.

BACKGROUND OF THE INVENTION

Stenosis is a narrowing or constriction of a duct or canal. A variety of disease processes, such as atherosclerotic lesions, immunological reactions, congenital abnormalities, and the like, can lead to stenosis of arteries or ducts. In the case of stenosis of a coronary artery, this typically leads to myocardial ischema. Percutaneous transluminal coronary angioplasty (PTCA), the insertion and inflation of a balloon catheter into a stenotic vessel to affect its repair is widely accepted as an option in the treatment of obstructive coronary artery disease. In general, PTCA is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall.

Other vascular invasive therapies include atherectomy (mechanical systems to remove plaque residing inside an artery), laser ablative therapy and the like. While the stenosis or occlusion is greatly reduced using these therapies, including PTCA, many patients experience a reoccurrence of the stenosis over a relatively short period. Restenosis, defined angiograhpically, is the recurrence of a 50% or greater narrowing of a luminal diameter at the site of a prior coronary artery disease therapy, such as a balloon dilatation in the case of PTCA therapy. Additionally, researchers have found that angioplasty or placement of a stent in the area of the stenosis irritates the blood vessel causing rapid reproduction of the inner layer of blood vessel cells and restenosis through a mechanism called hyperplasia. Restenosis is a major problem which limits the long-term efficacy of invasive coronary disease therapies. In particular, an intraluminal component of restenosis develops near the end of the healing process initiated by vascular injury, which then contributes to the narrowing of the luminal diameter. This phenomenon is sometimes referred to as "intimal hyperplasia." In some instances, restenosis develops so rapidly that it may be considered a form of accelerated atherosclerosis induced by injury. Additionally, the rapid onset of restenosis is compounded by the lack of predictability to determine which patients, vessels, or lesions will undergo restenosis.

Although the mechanism of restenosis is not fully understood, clinical evidence suggests that restenosis results from a migration and rapid proliferation of a subset of predominately medially derived smooth muscle cells which is apparently induced by the injury caused by the invasive therapy. Such injury, for example, is caused by the angioplasty procedure when the balloon catheter is inflated and exerts pressure against the artery wall, resulting in media tearing. It is known that smooth muscle cells proliferate in response to mechanical stretch and stimulation by a variety of growth factors. It is believed that such proliferation stops one to two months after the initial invasive therapy procedure but that these cells continue to express an extracellular matrix of collagen, elastin and proteoglycans. Additionally, animal studies have shown that after balloon injury, denudation of endothelial cells occurs, followed by platelet adhesion and aggregation, and the release of platelet-derived growth factor (PDGF) as well as other growth factors. As mentioned above, this mass of tissue contributes in the re-narrowing of the vascular lumen in patients who have restenosis. It is believed that a variety of biologic factors are involved in restenosis, such as the extent of the injury, platelets, inflammatory cells, growth factors, cytokines, endothelial cells, smooth muscle cells, and extracellular matrix production, to name a few.

It has been found that irradiating the blood vessel walls at the point of the stenosis will reduce or prevent hyperplasia Precise control over the amount of radiation is important, since insufficient radiation will not prevent hyperplasia and excessive radiation can damage the blood vessel. For other diagnostic or treatment purposes, it is also often desirable to introduce a small radiation source into a body vessel such as a coronary artery. Simply inserting a wire with a source secured in the wire at or near the distal end is effective in some cases. However, the wire will tend to lie along one side of the vessel, so that the near side receives significantly more radiation than the opposite, distant side. The near side could receive excessive, damaging, radiation exposure before the opposite side received the desired dose Such a non-centering, wire-carried, radiation source is shown by Dake et al. in U.S. Pat. No. 5,199,939 and Bradshaw in U.S. Pat. No. 5,643,171.

Zoumboulis, in U.S. Pat. No. 3,324,847, describes a catheter having a spherical inflatable chamber adjacent the catheter distal end. A fluid containing a radioactive material such as radioactive iodine is pumped into the chamber, inflating the chamber and treating the vessel walls with ionizing radiation. The chamber will stop blood flow, so it can be inflated for only a short period. Further, precisely controlling radiation exposure and fully draining the chamber to end treatment are very difficult.

A wire carrying a radioactive source could be inserted through a catheter lumen to the balloon location. The balloon would approximately center the source in the artery. However, since many guidewires extend mainly alongside the balloon catheter and balloons generally expand somewhat unevenly, the source would not be precisely centered. Further, irradiating a segment of an artery or the like generally requires some time, typically from about 3 to 45 minutes. Since a conventional angioplasty balloon substantially shuts off blood flow through the artery, treatment can be conducted for only short periods before damage from lack of blood flow becomes significant.

Liprie, in International Patent Application Publication Number WO95/26851 describes a device for treating a vessel occlusion with radiation in which a ribbed balloon catheter is inserted into a body vessel and inflated to provide perfusion between the ribs and a wire carrying a radiation source is inserted into a lumen extending into the balloon area. This positions the radiation source generally near the center of the vessel. However, as disclosed, the lumen has a much greater inside diameter than the outside diameter of the source wire, so that the source will generally be off center, in contact with the lumen wall. This will result in uneven irradiation of the vessel wall on opposite sides.

Other ribbed arrangements, using a double spiral rib or circumferential ribs are disclosed by Bradshaw et al. in U.S. Pat. No. 5,643,171 for centering a treatment lumen in a body vessel. While useful, the lobes may not provide precise centering, especially if the treatment wire is not a good fit in the lumen.

Teirstein in U.S. Pat. No. 5,540,659 describes a series of centering wire loops for centering a wire-carried radiation source in a body vessel. The generally oval shape of the wire loops and the complexity of inserting and removing the loop device make this arrangement less than fully effective. Teirstein also shows in his FIGS. 5 and 6 an embodiment using flexible wires that can be expanded away from a central catheter. However, the use of a single set of wires extending from the distal to proximal ends of the treatment zone will tend to allow the catheter to tilt relative to the wires. Also this system does not allow the use of multiple sets of expansion wires that could be opened independently.

A series of approximately spherical balloons are used to center a radiation source in the arrangement of Verin et al. as disclosed in European Patent Application No. 94109858.4. Although the source is centered in the vessel, lack of perfusion of blood past the site would permit only very short treatment times.

Ciamacco, in pending patent application Ser. No. 09/067,524 (Attorney Docket No. P-7770, filed Apr. 28, 1998) describes an apparatus for delivery of radiation in vivo. A device includes a seal located proximal to a balloon through which a cavity of the balloon is inflated with a composition including a radioactive compound. The seal includes a passage therethrough which provides the only access to the balloon cavity and terminates at the proximal end of the balloon. The passage through the seal provides fluid communication with an inflation lumen within the medical device lumen, wherein a ratio of an inner diameter of the inflatable member to an inner diameter of the inflation lumen is about 0.5 or greater. In such a construction, inflation and evacuation can be accomplished without contamination of the entire medical device lumen. Thus, substantially all of the solution including the radioactive compound can be evacuated from the balloon cavity after treatment due to the positioning of the passage in the seal. However, because there is only one access to the balloon cavity, inflation of the balloon with the radioactive composition and the subsequent flushing of the balloon with a non-radioactive composition can only be accomplished though a single lumen which requires vacuum pressure to remove the compositions. This, in turn, likely increases the time and the volume of radioactive waste generated to decontaminate the device.

Inplantable devices are also known for delivery of radiation in vivo that typically are an intra-arterial stents fabricated from either a pure metal or a metal alloy which has been irradiated so that is has become radioactive. However, as with any isotopes or radioactive material, the useful life, which includes both the shelf-life and the therapeutic life, of the device is limited by the half-life of the isotope utilized. The shelf-life of any device containing a radioactive material necessarily begins upon attachment of the radioisotope to the device because the radioactive material is continuously decaying. If storage and/or shipping are required, the radioactive material continues to decay to the point where any radiation emitted from the device is negligible. Thus, implantation of the device would not be advantageous.

Thus, there is a continuing need for improved devices for carrying a radiation source to a desired in vivo site that can be easily and accurately inserted into and removed from even very small vessels and which accurately center the source in the vessel while permitting effective perfusion so that treatment can be conducted over reasonably long periods. Additionally, there is a continuing need for such a device that can be subsequently decontaminated of radioactivity relatively easily.

SUMMARY OF THE INVENTION

It is an object of the invention to provide a device for delivering localized radiation in vivo. Preferably, a device according to the invention is capable of delivering localized radiation to a body lumen to treat or to prevent injury. The term "injury" means a trauma, that may be incidental to surgery or other treatment methods including deployment of a stent, or a biologic disease, such as an immune response or cell proliferation caused by the administration of growth factors. In addition, the methods of the present invention may be performed in anticipation of "injury" as a prophylactic. A prophylactic treatment is one that is provided in advance of any symptom of injury in order to prevent injury, prevent progression of injury or attenuate any subsequent onset of a symptom of such injury. The present invention applies to the treatment of acute and chronic closure and reclosure of body lumens.

One aspect of the present invention provides a medical device comprising an elongated tubular member having an proximal end and a distal end and an inflatable member having a proximal end, a distal end, and a inflatable member wall defining a cavity therein. Also included are three lumen. An inflation lumen longitudinally extends substantially within the tubular member from the proximal end of the elongated tubular member to the distal end of the tubular member, wherein the inflation lumen terminates within the inflatable member. A guidewire lumen longitudinally extends substantially from a guidewire access port operatively connected to the elongated tubular member, to the distal end of the tubular member. A flushing lumen longitudinally extends substantially within the tubular member from the proximal end of the enlongated tubular member to the distal end of the tubular member, wherein the flushing lumen terminates at the proximal end of the inflatable member.

Preferably, the medical device according to the present invention further comprises a seal located at the proximal end of the inflatable member, wherein the seal includes a first passage providing access to the cavity of the inflatable member via the inflation lumen and a second passage providing access to the cavity via the flushing lumen. Additionally, a ratio of an inner diameter of the inflatable member to an inner diameter of the inflation lumen is about 0.5 or greater.

Advantageously, a device in accordance with the present invention limits the amount of radioactive material required to fill the device as the entire device lumen is not filled with the radioactive material. Rather, only the inflation lumen is required to be filled with radioactive material to subsequently fill the inflatable member (i.e., a balloon). It is therefore another object of the present invention to minimize radiation exposure to both the medical professional administering the treatment and the length of the catheter within the patient while, at the same time, maximizing exposure to the treatment site. Also, and significantly, a device according to the present invention allows for flushing or rinsing to remove substantially all of the radioactive material through a second lumen so that, again, the entire device is not exposed to the radioactive material.

Flushing the device can be accomplished using positive pressure to inflate the balloon with a non-radioactive composition through the inflation lumen The non-radioactive flushing composition is forced from the distal end of the balloon to the proximal end of the balloon. Because positive pressure can be utilized, the flushing composition is forced through the flushing lumen without requiring vacuum pressure. It is believed that decontaminating a device according to the present invention may require less time and generate less radioactive waste than decontaminating conventional devices. For example, flushing or rinsing that may be accomplished using a single lumen typically requires the non-radioactive composition to be filled and evacuated through the same lumen using vacuum pressure to withdraw the composition. Thus, advantageously, by providing a separate flushing lumen, flushing or rinsing of the medical device may be accomplished by supplying a non-radioactive composition under pressure in a continuous, controlled, and accurate manner.

Preferably, a medical device in accordance with the present invention includes a first flexible extension member located in proximity to the proximal end of the tubular member, wherein a lumen of the flexible extension member is in fluid communication with the inflation lumen. Additionally, a second flexible extension member can be located in proximity to the proximal end of the tubular member, wherein a lumen of the second flexible extension member is in fluid communication with the flushing lumen.

A medical device of the present invention may also include a manifold located in proximity to the proximal end of the tubular member, wherein the manifold having a first access port in fluid communication with the guidewire lumen, a second access port in fluid communication with the inflation lumen, and a third access port in fluid communication with the flushing lumen.

Another aspect of the present invention provides a catheter including a one piece tubular member having a proximal end, a distal end, and a lumen; and a balloon having a distal end, a proximal end, an outer surface, and an inner surface defining a cavity therein, the proximal end being attached to the tubular member in proximity to the distal end. A guidewire lumen is longitudinally disposed within the lumen of the tubular member and a seal is located in the proximal end of the balloon. The catheter also includes a delivery lumen longitudinally disposed within the lumen of the tubular member, wherein the delivery lumen is in fluid communication with the cavity of the balloon through the seal and a flushing lumen longitudinally disposed within the lumen of the tubular member, wherein the flushing lumen is in fluid communication with the cavity of the balloon through the seal. Preferably, a flexible extension member is located in proximity to the proximal end of the tubular member, wherein a first lumen of the flexible extension member is in fluid communication with the delivery lumen and a second lumen of the flexible extension member is in fluid communication with the flushing lumen.

A manifold may also be integrally attached to the proximal end of the tubular member, wherein the manifold has a first access port in fluid communication with the delivery lumen and the flushing lumen, each via the flexible extension member respectively. Preferably, the manifold further includes a second access port in fluid communication with the guidewire lumen.

Yet another aspect of the present invention provides a system for in vivo delivery of radiation therapy comprising a radiation source; and a medical device operably linked to the radiation source. As indicated above, the medical device preferably includes an elongated tubular member having a proximal end and a distal end and an inflatable member having a proximal end, a distal end, and a inflatable member wall defining a cavity therein. An inflation lumen longitudinally extends substantially within the tubular member from the proximal end of the elongated tubular member to the distal end of the tubular member, wherein the inflation lumen terminates within the inflatable member. A flushing lumen longitudinally extends substantially within the tubular member from the proximal end of the elongated tubular member to the distal end of the tubular member, wherein the flushing lumen terminates at the proximal end of the inflatable member. A guidewire lumen longitudinally extends substantially from a guidewire access port operatively connected to the elongated tubular member to the distal end of the tubular member. Also included is a first flexible extension member located in proximity to the proximal end of the tubular member, wherein a lumen of the first flexible extension member is in fluid communication with the inflation lumen; and a second flexible extension member located in proximity to the proximal end of the tubular member, wherein a lumen of the second flexible extension member is in fluid communication with the flushing lumen. Preferably, the medical device further includes a seal located at the proximal end of the inflatable member, wherein the seal includes a first passage providing access to the cavity of the inflatable member via the inflation lumen and a second passage providing access to the cavity via the flushing lumen.

The system may further include a manifold integrally attached to the proximal end of the tubular member, wherein the manifold has a first access port in fluid communication with the lumen of the first flexible extension member and a second access port in fluid communication with the lumen of the second flexible extension member. Preferably, the manifold further comprises a third access port in fluid communication with the guidewire lumen. A flushing reservoir may also be included that is operably linked to the flushing lumen. In this instance, a manifold may preferably be located in proximity to the proximal end of the tubular member, wherein the manifold having a first access port in fluid communication with the guidewire lumen, a second access port operably linked to the radiation source, the second access port in fluid communication with the inflation lumen, and a third access port in fluid communication with the flushing reservoir.

Preferably, the seal in any device in accordance with the present invention is formed from a material selected from the group consisting of a thermoplastic material, a thermosetting material, and a combination thereof. More preferably, the seal is formed from a material selected from the group consisting of an anaerobic adhesive, an aerobic adhesive, and a radiation curable adhesive. In one embodiment, the seal is preferably formed from a material selected from the group consisting of a cyanoacrylate adhesive, an epoxy resin, and an acrylate adhesive.

In another embodiment, the seal extends substantially the length of the tubular member. In this embodiment, the seal is preferably formed from a material selected from the group consisting of a polyurethane, a silicone, a polyester, a polyolefin, a polyisobutylene, an acrylate, a vinyl halide polymer, a polyvinyl ether, a polyvinylidene halide, a polyacrylonitrile, a polyvinyl ketone, a polyvinyl aromatic polymer, a polyvinyl ester, a polyamide, a polycarbonate, a polyimide, an epoxy resin, an alkyd resin, a polyoxymethylene, a polyamide/polyether block copolymer, and a combination thereof.

In any embodiment of the present invention, the guidewire access port may be a single operator exchange port.

A further aspect of the present invention is a method for delivering localized radiation in vivo which includes the steps of providing a catheter; positioning the catheter in proximity to a desired in vivo location; and inflating the balloon with a solution including a radioactive material through the delivery tube. Preferably, the catheter includes a one piece tubular member having a proximal end, a distal end and a lumen and a balloon having a distal end, a proximal end and a wall defining a cavity therein, the proximal end being sealed to the tubular member. A guidewire lumen is longitudinally disposed within the tubular member from the proximal end to the distal end. Also included is a seal having a first passage and a second passage therethrough, wherein the seal sealingly engages the distal end of the tubular member to the proximal end of the balloon A delivery lumen is longitudinally disposed within the tubular member, wherein the delivery lumen is in fluid communication with the cavity of the balloon through the first passage in the seal; and a flushing lumen is longitudinally disposed within the tubular member, wherein the flushing lumen is in fluid communication with the cavity of the balloon through the second passage in the seal that terminates at the proximal end of the balloon.

The method may further include the steps of allowing at least a portion of an outer surface of the wall of the balloon to contact the desired in vivo location for a time sufficient to deliver a desired radioactive dose; and evacuating the solution including a radioactive material from the balloon through the flushing lumen. Preferably, the method includes the step of flushing the balloon with a non-radioactive material through the flushing lumen.

According to the present invention, radiation treatment can be effectively delivered in vivo so that a minimum volume of a radioactive solution is utilized while simultaneously completely filling the treatment balloon, thus minimizing exposure of patient tissue along the entire length of the catheter tube to radiation that may be emitted therefrom. Additionally, because the apparatus is provided with a flushing tube, substantially all the radioactive solution can be recovered once treatment is completed and the residual radioactivity can be flushed or rinsed from the device to effectively decontaminate the device. Accordingly, because smaller amounts of radioactive material are required, the inflation, evacuation, and decontamination of the device is relatively under control and the likelihood of contaminating the peripheral treatment area is minimized during treatment.

Yet another aspect of the present invention provides a use of a medical device for delivering in vivo radiation therapy comprising the steps of positioning a medical device in an in vivo treatment location; inflating the inflatable member with a radioactive composition through the inflation lumen; evacuating the radioactive composition from the inflatable member through the flushing lumen after treatment of the in vivo treatment location; and rinsing the inflatable member with a non-radioactive composition through the flushing lumen, wherein rising reduces an amount of radioactivity to a level substantially close to a background level. As indicated above, preferably the medical device includes an elongated tubular member having an proximal end and a distal end and an inflatable member having a proximal end, a distal end, and a inflatable member wall defining a cavity therein. An inflation lumen longitudinally extends substantially within the tubular member from the proximal end of the elongated tubular member to the distal end of the tubular member, wherein the inflation lumen terminates within the inflatable member. A guidewire lumen longitudinally extends substantially from a guidewire access port operatively connected to the elongated tubular member to the distal end of the tubular member. A flushing lumen longitudinally extends substantially within the tubular member from the proximal end of the enlongated tubular member to the distal end of the tubular member, wherein the flushing lumen terminates at the proximal end of the inflatable member.

Although catheters, in general, are well suited for the treatment of coronary arteries, any body lumen can be treated by a medical device of the present invention, including the vas deferens, ducts of the gallbladder, prostate gland, trachea, bronchus and liver or larger arteries such as the renal and carotid. The body lumens range in diameter from small coronary vessels of 3 mm or less to 28 mm in the aortic vessel.

BRIEF DESCRIPTION OF THE DRAWINGS

FIG. 1C is an enlarged partial longitudinal cross-section of a manifold interface with a device in accordance with the present invention;

FIG. 1D is an enlarged partial longitudinal cross-section of an extension tubing port in accordance with the present invention;

FIG. 2 is an exploded partial longitudinal cross-section of a balloon area of a medical device in accordance with the present invention;

FIG. 3 is a longitudinal cross-section of one embodiment of a medical device in accordance with the present invention;

DETAILED DESCRIPTION OF THE PREFERRED EMBODIMENTS

A medical device is provided by the present invention that allows for in vivo radiation delivery. Preferably, the medical device is a catheter having a seal located proximal to the balloon through which a cavity of the balloon is inflated with a composition including a radioactive compound. More preferably, the seal includes a first and a second passage therethrough. These passages provide limited access to the balloon cavity. One passage preferably terminates at the proximal end of the balloon, while the second passage terminates within the balloon. Thus, substantially all of the solution including the radioactive compound can be evacuated from the balloon cavity after treatment due to the positioning of the first passage in the seal. Even more preferably, the first passage through the seal is in fluid communication with a flushing lumen within the catheter lumen such that evacuation and flushing or rinsing can be accomplished without contamination of the entire catheter lumen. The second passage through the seal is in fluid communication with the inflation lumen such that filling the balloon with the radioactive material is accomplished without contamination of the entire device. Flushing or rinsing can be accomplished relatively easily because a small amount of a non-radioactive (i.e., cold) solution can be used to dilute the radioactive compound and a radiation safety officer can verify its subsequent disposal as medical waste (as opposed to radioactive medical waste) at the treatment site. Therefore, there is a relatively small amount of residual radioactivity within the catheter and subsequent contamination of the patient, medical personnel, and treatment area is minimized upon evacuation of the radioactive solution and subsequent withdrawal of the catheter from the patient.

Figure 1A:
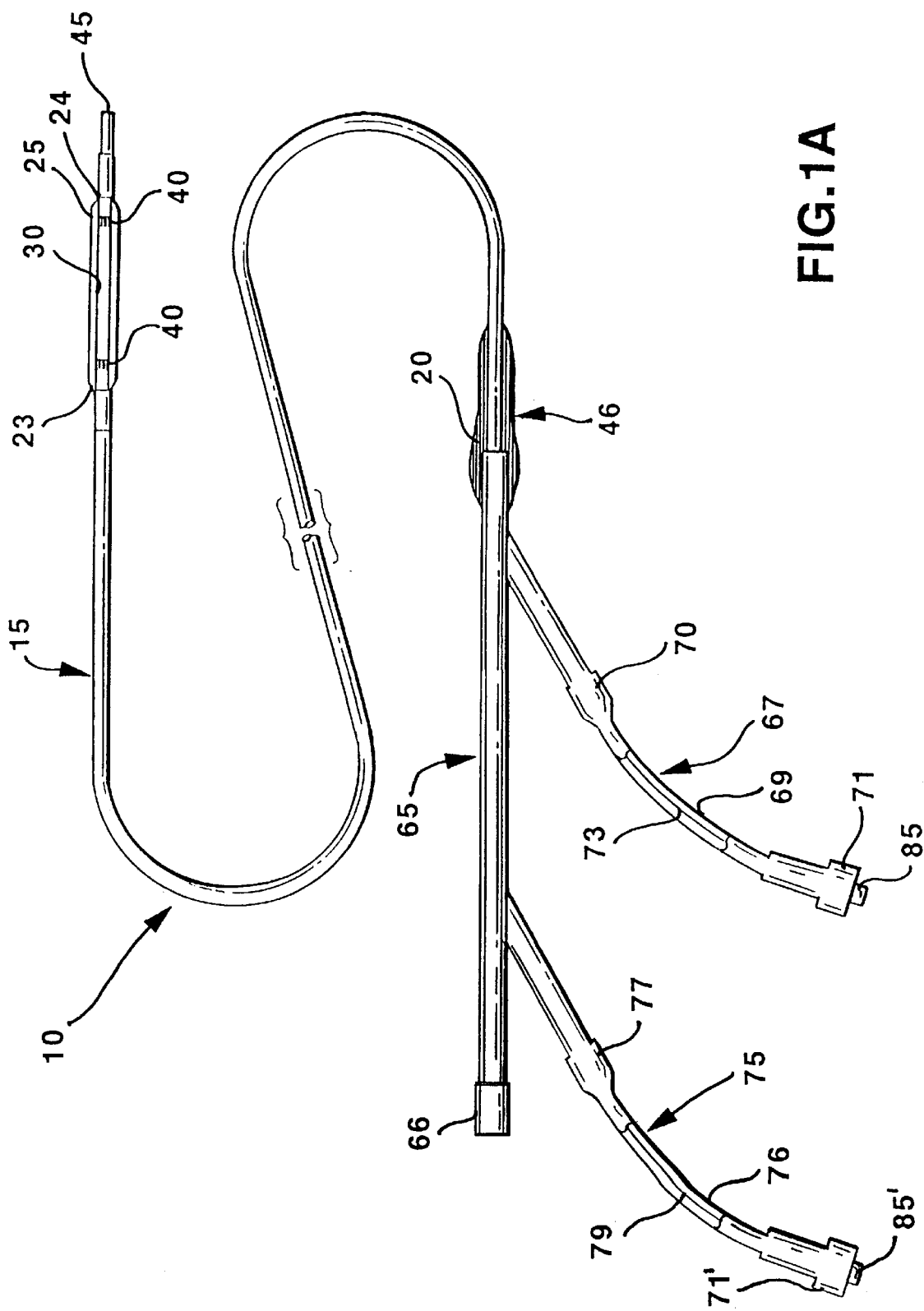
FIG. 1A is a side elevational view of one embodiment of a medical device in accordance with the present invention.
Figure 3C:
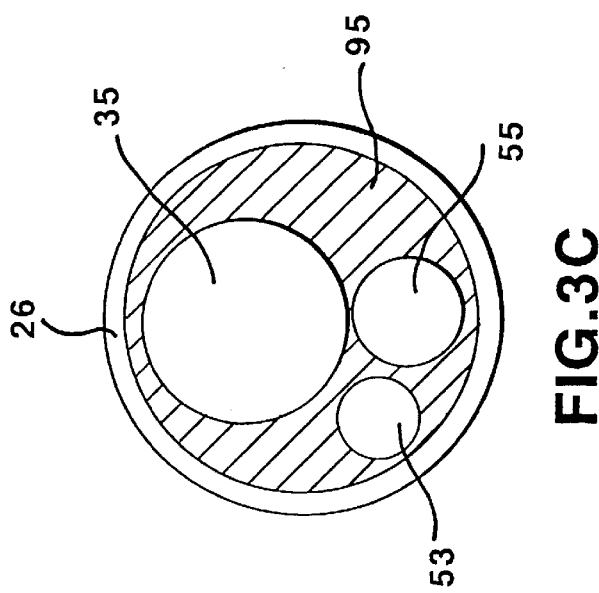
FIG. 3C is a transverse cross-sectional view taken across line B—B of another embodiment shown in FIG. 3.
Figure 3B:
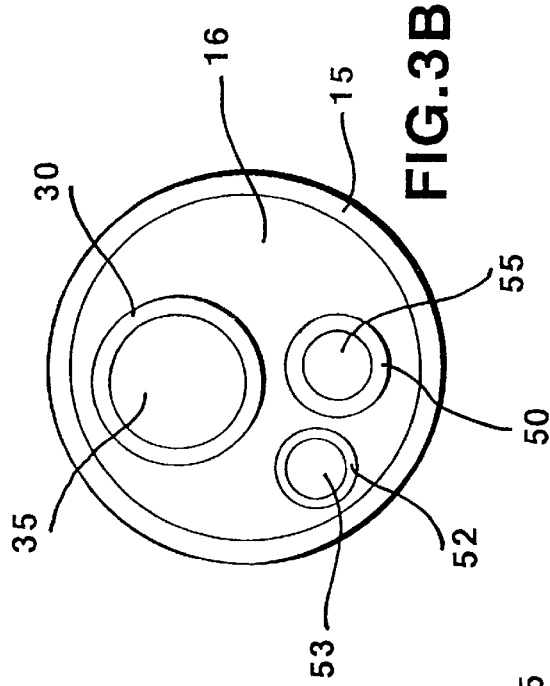
FIG. 3B is a transverse cross-sectional view taken across line B—B of one embodiment shown in FIG. 3.

Referring to FIG. 1A, a catheter 10 includes an elongated catheter wall 15 forming a catheter lumen 16 therein (as illustrated in detail in FIG. 3B). The catheter 10 includes a proximal end 46 operatively connected to a manifold 65 and a distal end which terminates with a distal end 45. A guidewire tube 30 (shown in detail in FIG. 2) extends longitudinally within the catheter wall 15 from the proximal end 46 to the distal end 45. A balloon 25 is located in proximity to the distal end of the catheter 10. As shown in FIG. 2. the balloon 25 includes a balloon wall 26 defining a balloon cavity 28 therein. The catheter wall 15 is open at the proximal end and extends distally toward the proximal end of the balloon 23 and preferably terminates at the proximal end of the balloon 23. Preferably, the proximal end of the balloon 23 is configured so there is no access to the balloon cavity 28 through the balloon wall 26, preferably by attaching the balloon wall 26 to the catheter wall 15. This can be accomplished by, for example, heat shrinking the balloon wall 26 about an outer surface of the catheter wall 15 or by application of a conventional biocompatible polymeric material such as a thermoplastic or a thermoset material between the balloon wall 26 and the outer surface of the catheter wall 15. In one preferred embodiment, the balloon is attached to the outer surface of the catheter wall 15 forming a balloon cavity 28 between the proximal end 23 of the balloon attached to the catheter wall 15 and the distal end 24 of the balloon attached to a guidewire tube 30, thus forming the balloon cavity 28 therein.

The guidewire tube 30 is preferably open at the distal end and preferably terminates beyond the distal end of the balloon 24. Preferably, the balloon wall 26 is preferably attached to the guidewire tube wall 30 by heat shrinking, gluing, bonding, or brazing, for example. More preferably, there is preferably no communication between the guidewire lumen 35 and the balloon cavity 28. The guidewire tube 30 provides a passage through which a guidewire (not shown) is positioned. The guidewire provides sufficient stiffness which improves the structural integrity of the catheter so that it can be pushed and turned though a tortuous body pathway, such as an artery or a vein, into a desired in vivo location, The guidewire can be made of any biocompatible material which can impart the desired stiffness, such as #304 stainless steel, a nickel-titanium alloy, or polyethylene, for example.

Figure 1B:
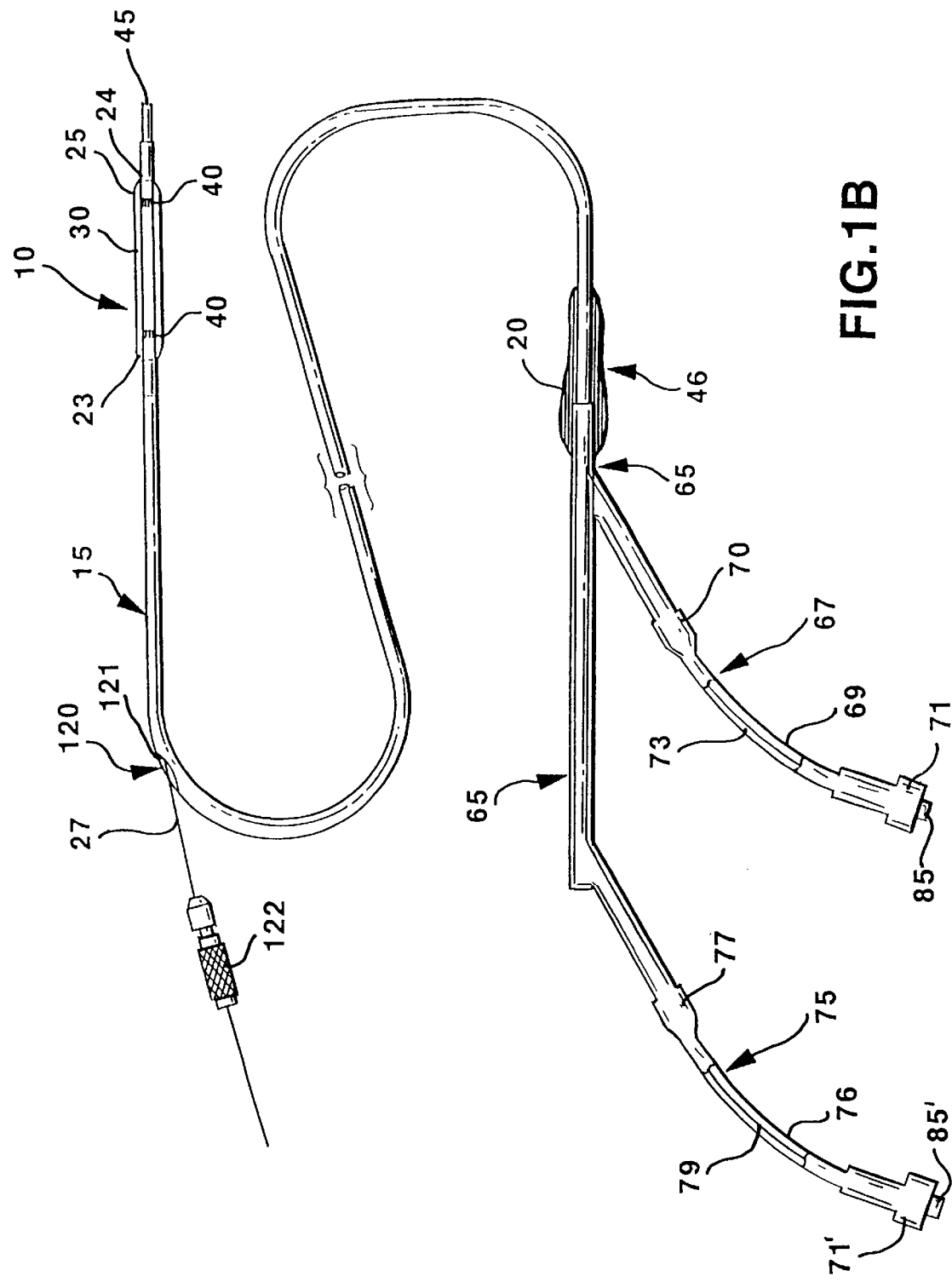
FIG. 1B is a side elevational view of another embodiment of a medical device in accordance with the present invention.

A medical device according to the present invention may also be provided with a conventional single operator exchange ("SOE") or "rapid exchange" access, as shown in FIG. 1B. In general, long wires are difficult to handle because such procedures require two operators who must be in communication during the procedure, requiring more time and increases the likelihood of contamination by dropping the guidewire from the sterile field, for example. Thus, medical devices having SOE access include a relatively shorter guidewire lumen that enables the physician to anchor or hold the guidewire when the catheter is removed from the body with the exchange occurring over the shorter guidewire lumen.

Referring now to FIG. 1B, an in vivo radiation delivery device including an SOE access is shown. The SOE access 120 is typically located at such a point along the length of the catheter so as to minimize the guidewire length necessary to position the balloon portion of the medical device in close proximity to the treatment site, such as about 20 cm from the distal end 45 of the catheter 10. The SOE access 120 includes a catheter SOE access port 121 through which the guidewire 27 can be inserted into the guidewire lumen 35 (not shown in FIG. 1B). Thus, the catheter SOE access port 121 is preferably in communication with the guidewire lumen. A conventional torquer 122 can be secured to the guidewire 27 for rotating the guidewire 27 during operation, as is known in the art. Advantageously, the SOE access 120 allows for relatively rapid removal of the catheter by the operator by grasping the guidewire 27 at a position proximal to the SOE access 120 after the torquer 122 has been removed. Thus, by providing the SOE access 120, the guidewire port 66 (and the respective portion of the manifold) is not needed in a device according to the present invention.

In any embodiment of the present invention, the manifold 65 is preferably an integral component of catheter 10, i.e., the manifold 65 is integrally attached to the catheter 10 in that it cannot be removed from the catheter. Preferably, the manifold 65 includes an inflation extension 67 and a flushing extension 75. As shown in FIG. 1C, an inflation extension tubing lumen 73 is in fluid communication with the inflation lumen 55, i.e., the inflation extension tubing lumen 73 lumen is a substantial continuation of the inflation lumen 55. Also as shown in FIG. 1C, a flushing extension lumen 79 is in fluid communication with a flushing lumen 53, i.e., the flushing extension tubing lumen 79 is a substantial continuation of the flushing lumen 53.

In any embodiment of the present invention, the balloon wall 26 that forms the balloon cavity 28 is preferably a one piece structure. The balloon length is about 2 cm to about 4 cm and the diameter is about 1.0 mm to about 45 mm, depending upon the site to be irradiated using the medical device of the present invention. Advantageously, because substantially all of the radiation-containing material can be evacuated from the balloon cavity 28, larger balloons, i.e., those having a diameter of about 10 mm to about 45 mm, can be readily used in accordance with the present invention. While a diameter range has been given, it will be appreciated by those skilled in the art that the diameter of the balloon should be as large as is practical given the vessel or passage way through which the balloon must pass to the site of radiation administration. It is to be further understood that the closer the balloon wall is to the body tissue at the treatment site, the more accurate the delivered dosage can be, the treatment time can be shortened, and the specific activity of the radioactive material can be lower, all of which are of benefit to the patient.

As mentioned above with respect to the relationship between the proximal end of the balloon to the catheter wall, the balloon distal end 24 is similarly attached to the guidewire tube 30 near the distal end 45 of the catheter 10. Again, suitable methods for attaching the balloon distal end 24 to the guidewire tube 30 include, for example, heat shrinking, gluing, bonding, or brazing.

A radiopaque marker 40 is bonded to the guidewire tube 30 at any location or more than one location along the length of the guidewire tube 30. Preferably, at least one location of the radiopaque marker 40 is within the balloon 25, such as the proximal end 23 and/or the distal end 24 of the balloon 25. The radiopaque marker 40 is used to provide a fluoroscopic indication of the location of the balloon 25 thus, allowing the operator to adjust the position of the balloon 25. Preferred materials are those that have a preferred density of about 19.3 gm/cm$^3$ to about 21.0 gm/cm$^3$. Preferred materials included in the marker 40 are typically a metal or a metal alloy. Suitable metals can be selected from the group of gold, iridium, to name a few. A suitable metal alloy can be selected from the group of a platinum-iridium alloy that can include, for example, 90% platinum and 10% iridium.

In the present invention, the catheter wall 15, the balloon wall 26, guidewire tube 30, the delivery tube 50, and a flushing tube 52 are each preferably formed from any material that is biocompatible, biostable, and minimizes irritation to the body passageway during treatment. Such a material may be a polymer, a metal, or a combination thereof. Biocompatible and biostable polymers are those which stimulate a relatively low chronic tissue response. Preferably, the polymer material is radiolucent and may be clear. Suitable polymers can be selected from the group of a polyurethane, a silicone, a polyester, a polyolefin, a polyisobutylene, an acrylate, a vinyl halide polymer (e.g., polyvinyl chloride), a polyvinyl ether (e.g., polyvinyl methyl ether), a polyvinylidene halide (e.g., polyvinylidene fluoride), a polyacrylonitrile, a polyvinyl ketone, a polyvinyl aromatic polymer (e.g., polystyrene), a polyvinyl ester (e.g., polyvinyl acetate), a polyamide, a polyearbonate, a polyimide, an epoxy resin, an alkyd resin, a polyoxymethylene, a polyamide/polyether block copolymer, and a combination thereof.

Each of the walls listed above can also be made from a metal such as stainless steel or a metal alloy such as a nickel-titanium alloy. Each of the walls listed above can be made from the same or different materials or it can be a multilayer construction, For example, a wall could include a polymeric outer wall surface and a metallic inner wall surface. Preferred embodiments of the present invention include polymeric materials such as polyamide, polyurethane, and/or a polyamide/polyether block copolymer (such as that commercially available under the trade designation PEBAX®, from Elf Atochem Corporation, Philadelphia, Pa.) for any of the walls including the catheter wall, the guidewire tube, the inflation tube, and the balloon wall. Typically, the guidewire (not shown) and the radiopaque markers 40 are typically not clear.

Typical size ranges for diameter dimensions are the following for each lumen type: preferably a catheter includes an inner diameter (i.e., forming the catheter lumen) of about 1.0 mm (0.039 inch) and an outer diameter of about 17 mm (0.065 inch). A guidewire tube typically includes an inner diameter in which a guidewire can be maneuvered. Accordingly, a guidewire tube preferably includes an inner diameter of about 0.30 mm (0.012 inch), about 0.41 mm (0.016 inch), or about 0.53 mm (0.021 inch) for guidewires having a diameter of about 0.25 mm (0.010 inch), about 0.26 mm (0.014 inch), or about 0.46 mm (0.018 inch), respectively, depending upon the application. For example, the smaller diameter may be used in neurovascular applications, while the larger diameter may be used in coronary applications. The inflation tube preferably includes an inner diameter of about 2 mm (0.078 inch) or less, more preferably about 0.30 mm (0.012 inch). Therefore, a medical device preferably includes a ratio of a balloon inner diameter to inflation lumen inner diameter of about 0.5 or greater.

Preferably, however, the flushing lumen 53 should be as large as would be accommodated by the catheter lumen 16. In so doing, decontamination can be accomplished as rapidly as possible given the finite dimensions of the catheter lumen 16.

For operator convenience, a manifold 65 is typically attached to a proximal end 46 of the catheter, as discussed above. The manifold 65 contains a plurality of access ports. One preferable port is a guidewire port 66, which provides access to the guidewire tube lumen 35. During a procedure, a guidewire (not shown in FIG. 1A) is inserted through the guidewire port 66 and into the guidewire tube lumen 35 so that the guidewire provides stiffness when the catheter 10 is inserted into a tortuous pathway to the desired treatment location.

Additionally, for operator convenience, a femoral marker or brachial marker (not shown) may be included a specified distance from the distal tip of the catheter which provides indication to the operator of the catheter position based on position of the marker external to the patient body. For example, a femoral marker is typically located about 100 cm from the distal tip of the catheter. Such a marker can be of any readily observable material such as paint, ink, and the like.

In any embodiment of the present invention, the manifold 65 includes an inflation access extension 67 and a flushing access extension 75. Preferably, the inflation access extension 67 includes an inflation extension tubing 69, which can be of any desired length. Similarly, the flushing access extension 75 includes a flushing extension tubing 76, which can also be of any desired length. For example, a cardiologist typically performs the portion of the procedure that requires manipulation of the guidewire through the guidewire port. Generally, this portion of the procedure is performed in a sterile field. A radiology or nuclear medicine specialist typically administers the radioactive composition through the access extension 67, which may or may not be in a sterile field. Thus, the extension tubing 69 may be sufficiently long so as to separate the sterile field from the non-sterile field. Such a separation tends to reduce the likelihood of contamination of the sterile field. Advantageously, by providing the inflation extension tubing, a radioactive source (i.e., the location of the radioactive composition prior to administration) can be removed from the procedure site and the patent. A remote location of the radioactive source can decrease the likelihood of unwanted radioactive contamination in the procedure site. Further, because the extension tubing 69 is preferably flexible and sufficiently long, more freedom of movement can be provided for the administration of the radioactive composition.

Evacuation of the radioactive composition is preferably accomplished through the flushing extension 75. As mentioned above, a separation between the patient and a bulk of the radioactive composition tends to reduce the likelihood of contamination of the sterile field. Advantageously, by providing the flushing extension tubing, a flushing reservoir (i.e., the location of a non-radioactive, "cold," composition during rinsing the device) can be removed from the procedure site and the patient. As the device is rinsed, the accumulated radioactive waste in a remote location can decrease the likelihood of unwanted radioactive contamination in the procedure site. Further, because the extension tubing 75 is preferably flexible and sufficiently long, more freedom of movement can be provided for the rinsing or flushing of the radioactive composition from the device. By flushing the device, substantially all the radioactivity can be removed such that the device can now be rendered "non-radioactive," i.e., having an amount of radiation substantially close to a background level. One with ordinary skill in the art will readily appreciate that acceptable background levels are dependent upon several variables such as geographic location and "safe" levels as determined by radiation safety personnel. As used herein, "substantially close to a background level" refers to an amount of radiation considered acceptable and therefore "cold" by radiation safety personnel.

Preferably, the inflation extension tubing 69 is connected at its distal end to the manifold via an inflation extension tubing adapter 70. The inflation extension tubing 69 also includes an extension tubing port 71 that provides access to the inflation extension tubing lumen 73. Preferably, the extension tubing lumen 73 is in fluid communication with the inflation tube lumen 55. Therefore, the inflation access extension 67 is a substantial continuation of the inflation lumen 55 for administration of the radioactive solution.

Similarly and preferably, the flushing extension tubing 75 is connected at its distal end to the manifold via a flushing extension tubing adapter 77. The flushing extension tubing 75 also includes an extension tubing port 71' that provides access to the flushing extension tubing lumen 79. Preferably, the flushing tubing lumen 79 is in fluid communication with the flushing lumen 53, i.e., is a substantial continuation of the flushing lumen 53 for evacuation and rinsing of the radioactive solution.

In a preferred embodiment, a potted rim 85 (85')provides limited access to the inflation extension lumen 73 (the flushing extension lumen 79'). As is shown in FIG. 1D with respect to the inflation extension 67, the potted rim 85 provides a narrowed access which decreases the amount of radioactive solution required to fill the inflation tube lumen. The flushing extension 75 has a similar relationship with the potted rim 85' so that smaller amounts of non-radioactive solution are required to rinse and decontaminate the device. The potted rim 85 (85')is preferably formed from a material that is biocompatible and compatible with the radioactive solution (e.g., will not absorb the radioactive isotope, will not decompose upon exposure to the radioactive solution, and the like). Suitable materials include thermoplastic materials and thermoset materials, preferably such materials include epoxy compounds and cyanoacrylate compounds, to name a few.

Preferably, the flushing extension tubing lumen 73 has an inner diameter, preferably the same as that of the inner diameter of the flushing lumen 53.

A strain relief segment 20 can be provided so that it surrounds at least a distal portion of the manifold 65 connected to the proximal end 46 of the catheter wall 15 The strain relief segment 20 is preferably made from a compliant material, such as natural or synthetic rubbers, which prevents damage and kinking of the joint between the catheter and the manifold because the manifold is typically less compliant than the catheter.

One preferred relationship between the balloon 25 and the catheter wall 15 can be better understood with reference to FIG. 2. The catheter wall 15 extends distally to a seal 90. Preferably, the seal 90 sealingly engages the catheter wall 15, the guidewire tube 30, the inflation tube wall 50, and the flushing tube wall 52 at the balloon proximal end 23. More preferably, the seal 90 sealingly engages an inner surface of the catheter wall 15, an outer surface of the guidewire tube 30, an outer surface of the inflation tube wall 50, and an outer surface of the flushing tube wall 52 at the balloon proximal end 23.

Figure 3A:
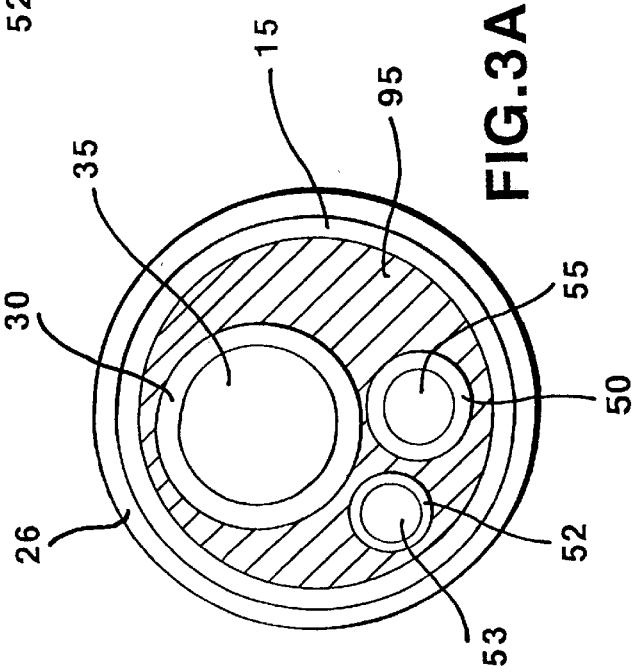
FIG. 3A is a transverse cross-sectional view taken across line A—A of the embodiment shown in FIG. 3.

The seal 90 is preferably formed from a potting material 95 (See, FIG. 3A). Typically, the potting material is a polymeric material that is biocompatible, biostable, and compatible with the radioactive solution (e.g., will not absorb the radioactive isotope, will not decompose upon exposure to the radioactive solution, and the like). Suitable materials are preferably selected from the group of a thermoplastic material, a thermosetting material, and a combination thereof. More preferably, the potting material is selected from the group of an anaerobic adhesive, an aerobic adhesive, and a radiation curable adhesive. Those skilled in the art will readily appreciate the nature of these adhesives which are conventionally defined as in the *Handbook of Adhesives*. edited by I. Skeist, ($3^{rd}$ ed., Chapman & Hall, N.Y., 1990), p. 7. Suitable examples include a cyanoacrylate adhesive (such as those commercially available under the trade designations LOCTITE® 4011, 4014, and 420 all from Loctite Corp., Hartford, Conn.; an epoxy resin (such as that commercially available under the trade designations 3311 and 3211, both from H. B. Fuller, St. Paul, Minn.), and an acrylate adhesive.

In one embodiment of the present invention shown in FIG. 3, an enlarged view of the proximal end of the balloon 25 sealingly engaged to the distal end of the catheter wall 15. The balloon 25 includes a balloon wall 26 that may be elastic or inelastic, preferably inelastic, forming a balloon cavity 28 therein. The balloon wall 26 is preferably made from a material selected from the group of polyethylene terephthalane, polyvinyl chloride, polyamide, polyurethane, a polyamide/polyether block copolymer, or other suitable medical grade materials for constructing relatively strong compliant devices. Although the balloon wall 26 is shown as a relatively smooth or uniform surface, it is within the scope of the present invention to include a balloon wall that may have undulations, indentations, rbs, protrusions, and the like, depending upon the desired radiation treatment to be delivered in vivo.

The seal 90 preferably provides limited access to the balloon cavity 28. As mentioned above, the balloon cavity 28 is in fluid communication with the inflation tube lumen 55 and the flushing tube lumen 53 through the seal 90. More preferably, the inflation tube lumen 55 and the flushing tube lumen 53 provide the only access to the balloon cavity 28. Even more preferably, the flushing tube lumen 53 terminates at the proximal end of the balloon (i.e., the distal end of the seal). Preferably, the inflation tube 50 terminates within the balloon cavity 28 and, more preferably, the inflation tube 50 terminates a distance equal to the diameter of the inflation tube 50 from the distal end of the balloon 24.

Preferably, the seal 90 is formed from a potting material 95, described above, as shown by a cross-section of the seal 90 in FIG. 3A. The seal 90 may be formed conventional application of the potting material to the desired location. In another embodiment, the seal runs the entire length of the catheter (FIG. 3C), wherein the catheter 10 may be formed as a single unit by mold injecting, as is known in the art. In this instance, the seal 90 is formed from a material that is suitable for forming the each of the tubes, as described above. Preferably, the seal is formed form a material selected from the group of a a polyurethane, a silicone, a polyester, a polyolefin, a polyisobutylene, an acrylate, a vinyl halide polymer (e.g., polyvinyl chloride), a polyvinyl ether (e.g., polyvinyl methyl ether), a polyvinylidene halide (e.g., polyvinylidene fluoride), a polyacrylonitrile, a polyvinyl ketone, a polyvinyl aromatic polymer (e.g., polystyrene), a polyvinyl ester (e.g., polyvinyl acetate), a polyamide, a polycarbonate, a polyimide, an epoxy resin, an alkyd resin, a polyoxymethylene, a polyamide/polyether block copolymer, and a combination thereof.

In one embodiment, the guidewire tube 30, the inflation tube 50, and the flushing tube 52 are all within the catheter lumen 16, as shown in the cross section depicted in FIG. 3B. In another embodiment shown in FIG. 3C, the potting material 95 (i.e., the seal 90) can extend substantially the entire length of the catheter lumen, as described above. In this embodiment, the guidewire lumen 35, the inflation lumen 55, and the flushing lumen 53 are still distinct from one another. This can be accomplished by an extrusion process which substantially simultaneously forms the guidewire lumen 35, the inflation lumen 55, and the flushing lumen 53. In contrast, the embodiment shown in FIG. 3B is typically accomplished by assembling individual tubes. If the assembly is multi-lumen extruded resulting in an embodiment as depicted in FIG. 3C, the proximal end of the balloon may be joined to the catheter as described above.

In operation, the catheter 10 is positioned in vivo, preferably following a vein or artery such that the balloon 25 is in close proximity to a desired in vivo location for exposure to radiation. A solution containing a radioactive material, typically an isotope, is introduced through the inflation access port 67 in the manifold 65. The radioactive solution flows from the inflation access port 67 through the inflation tube lumen 55 and into the balloon cavity 28. Preferably, the radioactive solution fills the balloon cavity 28 so as to inflate the balloon wall 26. The radioactive solution remains within the balloon cavity 28 for a desired period of time, depending upon the prescribed treatment dose.

In selecting the appropriate isotope to use in forming the radioactive material, typically in the form of an aqueous solution, several factors must be considered. For example, it is preferred that a low dose of radioactivity is delivered for a sufficient period of time to suppress the proliferative response to injury in vivo. Thus, total dose (generally measured in centi Gray) is typically determined by the specific activity of the radiation emitting material (generally measured in micro Curies ($\mu$Ci)) multiplied by time. However, the total dose must be balanced with the desired interruption of an injury response versus the detrimental mutagenic effect of tissue exposure to radiation. Thus, it is believed, for example, that $\gamma$-radiation would be considered relatively high intensity radiation so that administration over a long period of time would not be beneficial. Suitable radioactive materials include beta emitting isotope (e.g., $Sr^{90}$, $Yt^{90}$, or $P^{32}$) or gamma emitting isotope (e.g., an iridium isotope). Preferably, the solution contains a $\beta$-radiation emitting isotope. More preferably, the $\beta$-irradiation emitting isotope has a half-life of about 150 days or less. Most preferably, the solution contains a sterile aqueous solution of $Sr^{90}$ or $Yt^{90}$.

Once treatment is complete, the radioactive solution is then evacuated from the balloon cavity 28 through the flushing passage opening 54 (See, FIG. 2), through flushing lumen 53 to the flushing extension lumen 73 and exits through the flushing access port 71'. Typically, inflation and evacuation of the radioactive solution is accomplished with a syringe or a similar device. Preferably, the extension tubing port 71 is of a specified design that is only recognized by an adapter on a radioactive material inflation device so that cross-contamination is minimized. Similarly, the extension tubing port 71' is also of a specified design different from 71 that is only recognized by an adapter on a flushing device so that contamination is minimized. Because inflation of the balloon cavity is accomplished via inflation tube 50 and the evacuation and rinsing is accomplished via flushing tube 52, the entire catheter lumen 16 is not in contact with the radioactive solution and, subsequently, does not become contaminated with radioactivity. Accordingly, because less surface area is in contact with the radioactivity, the residual radioactivity (measured by cpm) remaining after evacuation of the radioactive solution is less than what would otherwise remain if the entire catheter lumen were exposed to the radioactive solution. Additionally, because of the size of the inflation tube lumen, a smaller volume of radioactive solution is required to be disposed of after treatment.

| No. | Component |
| --- | --- |
| 10 | catheter |
| 15 | catheter wall |
| 16 | catheter (interstitial) lumen |
| 20 | strain relief segment |
| 23 | proximal end of balloon |
| 24 | distal end of balloon |
| 25 | balloon |
| 26 | balloon wall |
| 27 | guidewire |
| 28 | balloon cavity |
| 30 | guidewire tube |
| 35 | guidewire lumen |
| 40 | radiopaque marker band(s) |
| 45 | distal end |
| 46 | proximal end |
| 50 | inflation (delivery) tube |
| 52 | flushing tube |
| 53 | flushing lumen |
| 54 | flushing opening |
| 55 | inflation lumen |
| 65 | manifold |
| 66 | guidewire port |
| 67 | inflation extension |
| 69 | inflation extension tubing |
| 70 | inflation extension tubing adapter |
| 71 | inflation extension tubing port |
| 71' | flushing extension tubing port |
| 73 | inflation extension tubing lumen |
| 75 | flushing extension |
| 76 | flushing extension tubing |
| 77 | flushing extension adaptor |
| 79 | flushing extension lumen |
| 85 | potted rim |
| 85' | potted rim |
| 90 | seal |
| 95 | potting material |
| 120 | SOE access |
| 121 | SOE catheter SOE access port |
| 122 | torquer |

The preceding specific embodiments are illustrative of the practice of the invention. The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to illustrative embodiments set forth herein.

What is claimed is:

1. A medical device, comprising:
   an elongated tubular member having an proximal end and a distal end;
   an inflatable member on said distal end of said elongated tubular member having a proximal end, a distal end, and a inflatable member wall defining a cavity therein;
   an inflation lumen longitudinally extending substantially within the tubular member from the proximal end of the elongated tubular member to the distal end of the tubular member, wherein the inflation lumen terminates within the inflatable member;

a guidewire access port operatively connected to said elongated tubular member;

a guidewire lumen longitudinally extending substantially from said guidewire access port to the distal end of the tubular member; and a flushing lumen longitudinally extending substantially within the tubular member from the proximal end of the enlongated tubular member to the distal end of the tubular member, wherein the flushing lumen terminates at the proximal end of the inflatable member.

2. The medical device of claim 1 further comprising a seal located at the proximal end of the inflatable member, wherein the seal includes a first passage providing access to the cavity of the inflatable member via the inflation lumen and a second passage providing access to the cavity via the flushing lumen.

3. The medical device of claim 1 wherein a ratio of an inner diameter of the inflatable member to an inner diameter of the inflation lumen is about 0.5 or greater.

4. The medical device of claim 1 further comprising a first flexible extension member located in proximity to the proximal end of the tubular member, wherein a lumen of the flexible extension member is in fluid communication with the inflation lumen.

5. The medical device of claim 4 further comprising a second flexible extension member located in proximity to the proximal end of the tubular member, wherein a lumen of the second flexible extension member is in fluid communication with the flushing lumen.

6. The medical device of claim 1 further comprising a manifold located in proximity to the proximal end of the tubular member, wherein the manifold having a first access port in fluid communication with the guidewire lumen, a second access port in fluid communication with the inflation lumen, and a third access port in fluid communication with the flushing lumen.

7. The medical device of claim 2 wherein the seal is formed from a material selected from the group consisting of a thermoplastic material, a thermosetting material, and a combination thereof.

8. The medical device of claim 2 wherein the seal is formed from a material selected from the group consisting of an anaerobic adhesive, an aerobic adhesive, and a radiation curable adhesive.

9. The medical device of claim 2 wherein the seal is formed from a material selected from the group consisting of a cyanoacrylate adhesive, an epoxy resin, and an acrylate adhesive.

10. The medical device of claim 1 wherein the guidewire access port comprises a single operator exchange port.

11. A catheter comprising:

a one piece tubular member having a proximal end, a distal end, and a lumen;

a balloon having a distal end, a proximal end, an outer surface, and an inner surface defining a cavity therein, the proximal end being attached to the tubular member in proximity to the distal end;

a guidewire lumen longitudinally disposed within the lumen of the tubular member;

a seal located in the proximal end of the balloon;

a delivery lumen longitudinally disposed within the lumen of the tubular member, wherein the delivery lumen is in fluid communication with the cavity of the balloon through the seal;

a flushing lumen longitudinally disposed within the lumen of the tubular member, wherein the flushing lumen is in fluid communication with the cavity of the balloon through the seal; and a flexible extension member located in proximity to the proximal end of the tubular member, wherein a first lumen of the flexible extension member is in fluid communication with the delivery lumen and a second lumen of the flexible extension member is in fluid communication with the flushing lumen.

12. The medical device of claim 11 further comprising a manifold integrally attached to the proximal end of the tubular member, wherein the manifold has a first access port in fluid communication with the delivery lumen and the flushing lumen, each via the flexible extension member respectively.

13. The catheter of claim 11 wherein the manifold further comprises a second access port in fluid communication with the guidewire lumen.

14. The catheter of claim 11 wherein the seal is formed from a material selected from the group consisting of a thermoplastic material, a thermosetting material, and a combination thereof.

15. The catheter of claim 11 wherein the seal is formed from a material selected from the group consisting of an anaerobic adhesive, an aerobic adhesive, and a radiation curable adhesive.

16. The catheter of claim 11 wherein the seal is formed from a material selected from the group consisting of a cyanoacrylate adhesive, an epoxy resin, and an acrylate adhesive.

17. The catheter of claim 11 wherein the seal extends substantially a length of the tubular member.

18. The catheter of claim 17 wherein the seal is formed from a material selected from the group consisting of a polyurethane, a silicone, a polyester, a polyolefin, a polyisobutylene, an acrylate, a vinyl halide polymer, a polyvinyl ether, a polyvinylidene halide, a polyacrylonitrile, a polyvinyl ketone, a polyvinyl aromatic polymer, a polyvinyl ester, a polyamide, a polycarbonate, a polyimide, an epoxy resin, an alkyd resin, a polyoxymethylene, a polyamide/polyether block copolymer, and a combination thereof.

19. The catheter of claim 11 wherein the catheter is a single operator exchange catheter.

* * * * *